US00PP17825P2

(12) United States Plant Patent
Bradford

(10) Patent No.: US PP17,825 P2
(45) Date of Patent: Jun. 26, 2007

(54) NECTARINE TREE NAMED 'MAY PEARL II'

(50) Latin Name: *Prunus persica*
Varietal Denomination: MAY PEARL II

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/311,241

(22) Filed: Dec. 20, 2005

(51) Int. Cl.
*A01H 5/00* (2006.01)

(52) U.S. Cl. ..... Plt./188
(58) Field of Classification Search ..... Plt./188
See application file for complete search history.

(56) References Cited

U.S. PATENT DOCUMENTS

PP9,099 P * 4/1995 Escande ..... Plt./188
PP9,107 P * 4/1995 Escande ..... Plt./188
PP14,248 P2 10/2003 Bradford
PP15,845 P2 7/2005 Bradford

OTHER PUBLICATIONS http://tess2.uspto.gov/bin/showfield?f=doc&state=aldc7a.2.2.*

* cited by examiner

*Primary Examiner*—Wendy Haas

(57) ABSTRACT

The present invention relates to a nectarine tree and more particularly to a new and distinct variety broadly characterized by a medium size, vigorous, half-hardy, self-fertile, productive and regular bearing tree that requires only 450 chilling hours. The fruit matures under the ecological conditions described in late May, with first picking on May 24, 2005. The fruit is uniformly medium in size, excellent in flavor, globose in shape, clingstone in type, firm in texture, white in flesh color, and mostly red in skin color. The variety was developed as a first generation cross using an unnamed white flesh peach as the selected seed parent and 'Rose Bright' (U.S. Plant Pat. No. 15,845) as the selected pollen parent.

1 Drawing Sheet

Botanical classification: *Prunus persica.*
Variety denomination: 'MAY PEARL II'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'MAY PEARL II'. The present variety was hybridized by me in 2001, grown as a seedling on its own root in my greenhouse, and transplanted to a cultivated area of my experimental orchard near Le Grand, Calif. in Merced County (San Joaquin Valley).

The variety was developed as a first generation cross using an unnamed white flesh peach (unpatented) as the selected seed parent and 'Rose Bright' (U.S. Plant Pat. No. 15,845) as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon when the present variety was compatible and true to type.

The present variety is very distinguished from its pollen parent, 'Rose Bright' (U.S. Plant Pat. No. 15,845) nectarine, by producing nectarines that are white instead of yellow in flesh color and that are sub-acid instead of acid in flavor.

The present variety is similar to 'Early Pearl' (U.S. Plant Pat. No. 14,248) nectarine, by producing nectarines that are firm in texture, sub-acidic and sweet in flavor, full red in skin color, and white in flesh color, but is distinguished therefrom by requiring less chilling hours, blooming earlier, and producing fruit that is somewhat larger in size and that has a sweet instead of bitter kernel.

SUMMARY OF VARIETY

In summary, the present variety is characterized by a medium size, vigorous, half-hardy, self-fertile, productive and regular bearing tree that requires only 450 chilling hours. The fruit matures under the ecological conditions described in late May, with first picking on May 24, 2005. The fruit is uniformly medium in size, sub-acidic and sweet in flavor, globose in shape, clingstone in type, firm in texture, white in flesh color, and mostly red in skin color.

DRAWING

The accompanying photograph exhibits four whole fruits positioned to display the characteristics of the skin color and form, one fruit divided transversely to the suture plane to reveal the flesh and stone, a typical leaf, a tip shoot with varying stages of leaf development, a typical stone, and an inset with a flower in full bloom.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on May 28, 2005, on the original tree during its fourth growing season. All major color code designations are by reference to the Inter-Society Color Council, National Bureau of Standards. Common color names are also used occasionally.

TREE

Size: Medium, reaching a height of 11' [3.35 m.] and a spread of 8' [2.44 m.] after four growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to a central leader shape.

Hardiness: Half-hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 450 hours.

Trunk:

*Size.*—Medium, with a maximum diameter of 3¾" [95 mm.] after the fourth growing season.

*Texture.*—Somewhat shaggy.

*Bark color.*—A two-tone variegation of Dark grayish reddish brown [47. d.gy.rBr] and Moderate brown [58. m.Br].

*Lenticels.*—Approximate Number Per Square Inch: 10. Color: Moderate orange yellow [71. m.OY]. Typical Size: ⅛" [3.2 mm.] to ⅜" [9.5 mm.]. Shape: Eye-shaped to elongated.

Branches:

*Size.*—Diameter of limb is 1⅜" [35 mm.] measured 12" from central leader.

*Texture.*—Smooth on 1st year wood, increasing roughness with age.

*Color.*—1st Year Wood Topside: Grayish red [19. gy.R]. 1st Year Wood Underside: Brilliant yellow green [116. brill.YG]. Older Wood: Deep yellowish brown [75. deep yBr].

*Lenticels.*—Approximate Number Per Square Inch. 50. Color: Light yellowish brown [76. l.yBr]. Typical size: 1/82" [0.8 mm.] to ⅛" [3.2 mm.]. Shape: Eye-shaped to elongated.

Leaves:

*Size.*—Medium. Average Length: 5 9/16" [141 mm.]. Average width: 1 11/16" [43 mm.].

*Arrangement.*—Alternate.

*Thickness.*—Medium.

*Form.*—Elliptical.

*Apex.*—Acuminate.

*Base.*—Rounded.

*Surface.*—Smooth.

*Color.*—Dorsal Surface: Dark yellowish green [137. d.yG]. Ventral Surface: Moderate yellowish green [136. m.yG].

*Margin.*—Finely serrate.

*Venation.*—Pinnately net veined.

*Petiole.*—Average Length: 7/16" [11.1 mm.]. Average Thickness: 1/16" [1.6 mm.]. Color: Brilliant yellow green [116. brill.YG].

*Stipules.*—Number: 2 per leaf, up to 6 per growing tip. Average Length: ⅜" [9.5 mm.]. Color: Light yellow green [119. l.YG] toward the tip and grayish red [19. gy.R] toward the base when young, Dark grayish reddish brown [47. d.gy.rBr] when old.

*Glands.*—Number: Usually 2, sometimes 4. Position: Oppositely positioned at the intersection of petiole and base of blade. Size: Small. Form: Globose. Color: Brilliant yellow green [116. brill.YG] on younger leaves turning Moderate yellowish brown [77. m.yBr] in the center with maturity.

*Leaf buds.*—Conic.

Flowers: Perfect, complete, perigynous, usually a single pistil, typically thirty or more stamens, five sepals and petal locations alternately positioned.

*Type.*—Showy, large.

*Average flower diameter.*—1¾" [44.5 mm.].

*Number of petals.*—Usually five, with extra petal fragments common, very few double blossoms.

*Petal shape.*—Circular to oval.

*Petal margin.*—Somewhat wavy.

*Average petal diameter.*—11/16" [17.5 mm.].

*Average petal length.*—¾" [19.1 mm.].

*Petal apex.*—Rounded.

*Petal base.*—Irregularly rounded.

*Petal color.*—Pale pink [7. p.Pk] toward the apex, Light purplish pink [249. l.pPk] toward the base.

*Anther color.*—Strong reddish orange [35. s.rO] over Light yellow [86. l.Y] centers at bloom onset.

*Stigma color.*—Light greenish yellow [101. l.gY].

*Sepal color.*—Dark purplish red [259. d.pR].

*Sepal length.*—¼" [6 mm.].

*Sepal width.*—3/16" [5 mm.].

*Average pistil length.*—11/16" [17.5 mm.].

*Average stamen length.*—⅝" [15.9 mm.].

*Fragrance.*—Moderate.

*Blooming period.*—Somewhat early compared to other varieties.

*Onset of bloom.*—One percent on Feb. 13, 2005.

*Date of full bloom.*—Feb. 22, 2005.

*Duration of bloom.*—One to two weeks, dependent on ambient temperature.

*Number per cluster.*—1 to 3 with single flowers most common.

FRUIT

Maturity when described: Firm ripe, May 28, 2005.

Date of first picking: May 24, 2005.

Date of last picking: Jun. 3, 2005.

Size: Uniform, medium.

*Average diameter axially.*—2¾" [69.9 mm.].

*Average diameter across cheek plane.*—2 11/16" [68.3 mm.].

*Average diameter across suture plane.*—2¾" [69.9 mm.].

*Typical weight.*—6.0 ounces [170 grams].

Form: Uniform, mostly symmetrical, globose.
*Longitudinal section form.*—Round to somewhat oval.
*Transverse section through diameter.*—Round.
Suture: A shallow groove extending from the base and terminating just beyond the pistil point with a slight depression, sharper near the base and near the apex.
Ventral surface: Rounded, lipped throughout.
Lips: Slightly unequal.
Cavity: Flaring, circular, slightly elongated in the suture plane, suture showing on one side, Pale greenish yellow [104. p.gY] stem markings typical.
*Depth.*—7/16 [11.1 mm.].
*Breadth.*—15/16" [23.8 mm.].
Base: Somewhat truncate, slightly cordate if viewed parallel to suture.
Apex: Rounded.
Pistil point: Both apical and oblique, very short 1/32" [0.8 mm.], depressed within the suture.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—Slight in wet season.
*Color.*—Dark red [16. d.R] smoothly blending into a Deep reddish orange [36. deep rO] background with slight Brilliant orange yellow [67. brill.OY] freckling toward the apex.
Flesh:
*Color.*—White [263. White] to Pale yellow green [121. p.YgG] with very slight Moderate red [15. m.R] flecking toward the skin.
*Surface of pit cavity.*—Pale greenish yellow [104. p.gY] fibers breaking when twisted from the stone.
*Amygdalin.*—Scarce.
*Juice.*—Abundant, rich.
*Texture.*—Firm, crisp, melting.
*Fibers.*—Abundant, fine.
*Ripens.*—Slightly earlier toward the apex.
*Flavor.*—Mildly sub-acidic and sweet, typically 14 brix.
*Aroma.*—Very slight.
*Eating quality.*—Excellent.

STONE

Type: Clingstone.
Form: Oval.
Hilum: Narrow, oblong.
Base: Straight, rounded.
Apex: Acute, with a 1/8" [3.2 mm.] tip with an average angle of 70 degrees.
Sides: Equal.
Surface: Irregularly to horizontally furrowed near the apex, lightly pitted toward the base, grooves present on each side of the dorsal fin.
Ridges: Jagged.
External color of stone: Light yellowish brown [76. l.yBr] when freshly removed.
Pit wall color when cracked: Pale orange yellow [73. p.OY].
Cavity surface color: Light orange yellow [70. l.OY].
Average pit wall thickness: 1/4" [6.4 mm.].
Average width: 15/16" [23.8 mm.].
Average length: 1 1/4" [31.8 mm.].
Average breadth: 11/16" [17.5 mm.].
Tendency to split: Slight.
Kernel:
*Form.*—Oval.
*Skin color.*—Pale yellow [89. p.Y] when freshly removed.
*Pellicle color.*—Grayish yellowish brown [80. gy.yBr] when freshly removed.
*Vein color.*—Light yellowish brown [76. l.yBr] when freshly removed.
*Taste.*—Sweet.
*Viable.*—Yes with embryoculture techniques.
*Average width.*—7/16" [11.1 mm.].
*Average length.*—3/4" [19.1 mm.].
*Amygdalin.*—Scant.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistant to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is similar to 'Early Pearl' (U.S. Plant Pat. No. 14,248) nectarine, by producing nectarines that are firm in texture, sub-acidic and sweet in flavor, full red in skin color, and white in flesh color, but is distinguished therefrom by requiring less chilling hours, blooming earlier, and producing fruit that is somewhat larger in size and that has a sweet instead of bitter kernel.

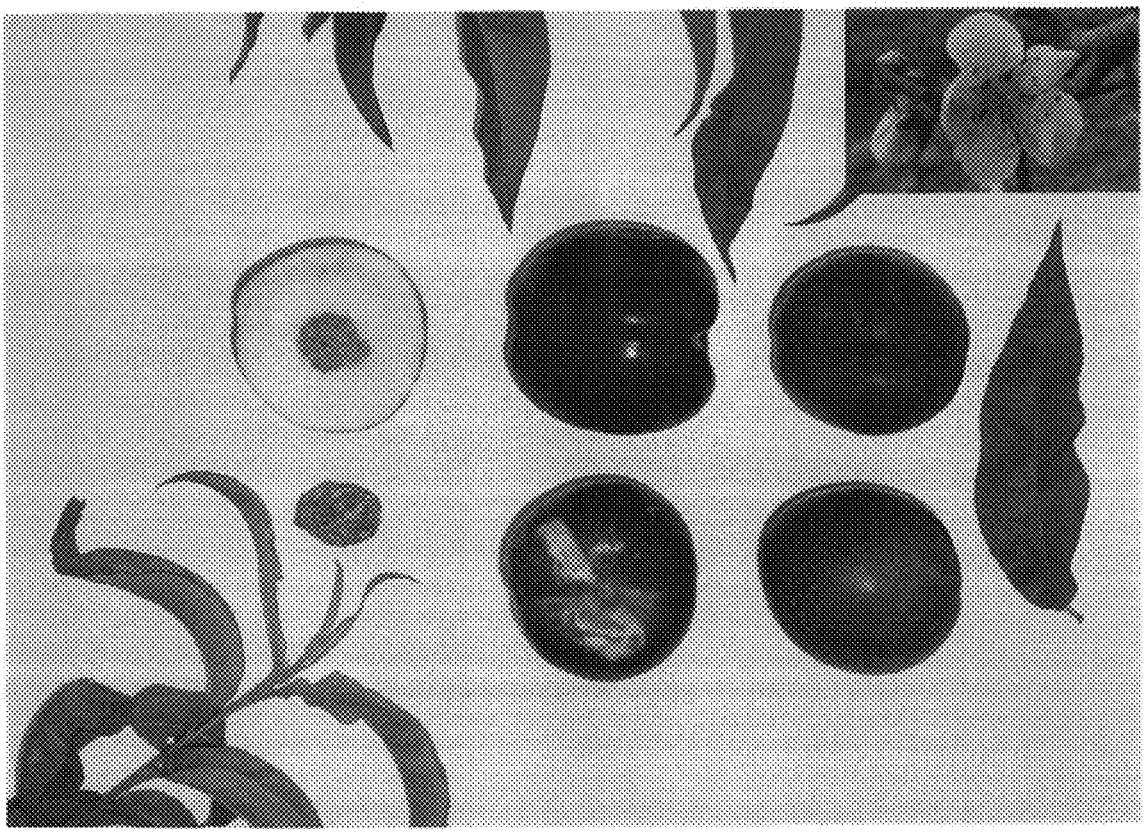

* * * * *